United States Patent
Metcalf

(10) Patent No.: US 12,161,608 B2
(45) Date of Patent: Dec. 10, 2024

(54) METHODS OF PREVENTING AND TREATING HEALTH CONDITIONS USING CANNABINOID ANIONS

(71) Applicant: NATURAL EXTRACTION SYSTEMS, LLC, Boulder, CO (US)

(72) Inventor: Douglas G. Metcalf, Boulder, CO (US)

(73) Assignee: Natural Extraction Systems, LLC, Boulder, CO (US)

(*) Notice: Subject to any disclaimer, the term of this patent is extended or adjusted under 35 U.S.C. 154(b) by 3 days.

(21) Appl. No.: 17/776,935

(22) PCT Filed: Nov. 13, 2020

(86) PCT No.: PCT/US2020/060313
§ 371 (c)(1),
(2) Date: May 13, 2022

(87) PCT Pub. No.: WO2021/097150
PCT Pub. Date: May 20, 2021

(65) Prior Publication Data
US 2022/0401382 A1   Dec. 22, 2022

Related U.S. Application Data

(60) Provisional application No. 62/969,613, filed on Feb. 3, 2020, provisional application No. 62/935,494, filed on Nov. 14, 2019.

(51) Int. Cl.
| | | |
|---|---|---|
| A61K 31/05 | (2006.01) | |
| A61P 1/12 | (2006.01) | |
| A61P 19/02 | (2006.01) | |
| A61P 25/04 | (2006.01) | |
| A61P 25/08 | (2006.01) | |
| A61P 25/20 | (2006.01) | |
| A61P 25/22 | (2006.01) | |

(52) U.S. Cl.
CPC .............. *A61K 31/05* (2013.01); *A61P 1/12* (2018.01); *A61P 19/02* (2018.01); *A61P 25/04* (2018.01); *A61P 25/08* (2018.01); *A61P 25/20* (2018.01); *A61P 25/22* (2018.01)

(58) Field of Classification Search
CPC ...................................................... A61K 31/05
See application file for complete search history.

(56) References Cited

U.S. PATENT DOCUMENTS

2019/0030170 A1* 1/2019 Kingsley .............. A61K 31/352

FOREIGN PATENT DOCUMENTS

| JP | 2014131114 A | * | 7/2014 | | |
| WO | WO-2014131114 A1 | * | 9/2014 | ............. | G01N 21/78 |

OTHER PUBLICATIONS

Bruni et al., Cannabinoid Delivery Systems for Pain and Inflammation Treatment, Molecules. Oct. 2018; 23(10): 2478.*
Starks, Michael, Marijuana Chemistry Genetics, Processing & Potency 2nd ed., (1993), pp. 1-199.*

* cited by examiner

*Primary Examiner* — Svetlana M Ivanova
(74) *Attorney, Agent, or Firm* — Douglas G. Metcalf

(57) ABSTRACT

Various aspects of this patent document relate to methods of administering cannabinoid anions to treat various health conditions.

20 Claims, No Drawings

METHODS OF PREVENTING AND TREATING HEALTH CONDITIONS USING CANNABINOID ANIONS

CROSS-REFERENCE TO RELATED APPLICATIONS

This patent application claims priority to U.S. Provisional Patent Application No. 62/935,494, filed Nov. 14, 2019, and U.S. Provisional Patent Application No. 62/969,613, filed Feb. 3, 2020, each of which is incorporated by reference in its entirety.

BACKGROUND

Cannabinoids are known to prevent and treat various health conditions. Pharmaceuticals containing cannabinoids nevertheless present known risks. A clinical trial of EPIDIOLEX®, for example, showed a dose-dependent increase in adverse events of 84% and 94% in patients receiving 10 and 20 milligrams of cannabidiol per kilogram body weight per day, respectively (Devinsky et al., NEW ENGLAND JOURNAL OF MEDICINE, 2018, 378:1888-1897). Improved pharmaceutical formulations could improve the efficacy and safety profiles of cannabinoid formulations.

SUMMARY

Various aspects of this patent document relate to a method to administer a cannabinoid anion to a subject to prevent or treat a health condition.

Cannabinoids are known to treat a wide range of health conditions. "Numerous diseases, such as anorexia, emesis, pain, inflammation, multiple sclerosis, neurodegenerative disorders (Parkinson's disease, Huntington's disease, Tourette's syndrome, Alzheimer's disease), epilepsy, glaucoma, osteoporosis, schizophrenia, cardiovascular disorders, cancer, obesity, and metabolic syndrome-related disorders, to name just a few, are being treated or have the potential to be treated by cannabinoid agonists/antagonists/cannabinoid-related compounds." (Kogan & Mechoulam, DIALOGUES IN CLINICAL NEUROSCIENCE 2007; 9(4):413-430). Numerous clinical trials demonstrate the effectiveness of cannabinoids at treating the health conditions described in this patent document including over 500 clinical trials listed on ClinicalTrials.gov. Thirty-three states of the United States and the District of Colombia of the United States enacted medical marijuana laws that recognize that cannabinoids can treat over 100 different conditions including acquired immune deficiency syndrome ("AIDS"), Alzheimer's disease, amyotrophic lateral sclerosis ("ALS"), anorexia, anxiety, Arnold-Chiari malformation, arthritis, autism, autism spectrum disorder, cachexia, cancer, causalgia, cerebral palsy, chemotherapy-induced anorexia, chronic back pain, chronic pain, chronic seizures, chronic traumatic encephalopathy, complex regional pain syndrome, complex regional pain syndrome type II, cramping, Crohn's disease, cystic fibrosis, debilitating psychiatric disorders, decompensated cirrhosis, diabetes mellitus, Dravet syndrome, dyskinetic movement disorders, dystonia, Ehlers-Danlos syndrome, elevated intraocular pressure, epidermolysis bullosa, epilepsy, fibromyalgia, fibrous dysplasia, glaucoma, headache, hepatitis C, Huntington's disease, hydrocephalus, hydromyelia, idiopathic pulmonary fibrosis, inclusion body myositis, inflammatory autoimmune-mediated arthritis, inflammatory bowel disease, inflammatory demyelinating polyneuropathy, interstitial cystitis, intractable epilepsy, intractable pain, intractable skeletal muscular spasticity, intractable spasticity, Lennox-Gastaut syndrome, lupus, migraines, mitochondrial disease, multiple sclerosis, muscle spasms, muscular dystrophy, myasthenia gravis, myoclonus, nail-patella syndrome, neural-tube defects, neurodegenerative diseases, neurofibromatosis, neurological disorders, neuropathic pain, neuropathy, obstructive sleep apnea, osteogenesis imperfecta, pancreatitis, Parkinson's disease, peripheral neuropathy, post herpetic neuralgia, post laminectomy syndrome, post-concussion syndrome, post-traumatic stress disorder ("PTSD"), psoriasis, psoriatic arthritis, reflex sympathetic dystrophy, renal failure requiring dialysis, residual limb pain, rheumatoid arthritis, seizure disorders, sickle cell anemia, sickle cell disease, Sjogren's syndrome, spasmodic torticollis (cervical dystonia), spasticity, spinal cord disease, spinal cord injury, spinal stenosis, spinocerebellar ataxia, syringomyelia, Tarlov cysts, Tourette's syndrome, traumatic brain injury ("TBI"), ulcerative colitis, and visceral pain. The United States Food & Drug Administration approved cannabinoids to treat four indications: anorexia in patients having AIDS, chemotherapy-induced nausea and vomiting, Dravet syndrome, and Lennox-Gastaut syndrome. The United States Patent & Trademark Office and every other major patent office has granted patents that recognize that cannabinoids can treat various health conditions described in this patent document.

Cannabinoid anions are generally more effective at treating health conditions than their conjugate acids, which are the conventional, molecular forms of cannabinoids. Without being bound by any specific theory, molecular cannabinoids tend to aggregate, which inhibits bioavailability, whereas cannabinoid anions repel each other, which increases bioavailability. The perceived onset of pharmaceutical effects caused by cannabinoid anions relative to their neutrally-charged conjugate acids suggests that cannabinoid anions are much more rapidly absorbed upon administration than their neutrally-charged conjugate acids, which increases bioavailability.

Cannabinoid anions can be produced from their conjugate acids by deprotonation with hydroxide, ethoxide, or other strong Brønsted base in a protic polar solvent such as ethanol as described, for example, in U.S. Pat. No. 10,555,914. Generally applicable methods to synthesize the conjugate acids of the cannabinoid anions described in this patent document have been described by numerous research groups including those lead by Alexandros Makriyannis, John W. Huffman, and Raphael Mechoulam. Reviews that catalog methods to synthesize the conjugate acids of various cannabinoid anions are prevalent and include CANNABIS AND CANNABINOID RESEARCH 2016; 1(1):90-101, which also catalogs known pharmaceutical properties of numerous cannabinoids and their derivatives.

Pharmaceutical compositions comprising cannabinoid anions may be formulated, for example, according to REMINGTON: THE SCIENCE AND PRACTICE OF PHARMACY, 22nd edition (Allen Jr, Loyd V., editor) Pharmaceutical Press, 2012. Pharmaceutical compositions should generally either lack any excipient that has a pKa of less than 8 or inhibit chemical communication between any such excipient and a cannabinoid anion.

A cannabinoid anion is generally at least as effective at treating the indications that its neutrally-charged conjugate acid is effective at treating. For example, 2-(6-isopropenyl-3-methylcyclohex-2-en-1-yl)-3-hydroxy-5-pentylphenolate is generally at least as effective at treating the indications that cannabidiol is effective at treating.

DETAILED DESCRIPTION

Various aspects of this patent document relate to a method to administer a cannabinoid anion, comprising administering a pharmaceutical composition comprising a cannabinoid anion to a subject who presents with either a health condition or a risk of developing a health condition, wherein the cannabinoid anion is not a carboxylate.

Various aspects of this patent document relate to a method to treat a health condition, comprising administering a pharmaceutical composition comprising a therapeutically effective amount of a cannabinoid anion to a subject who presents with the health condition, wherein the cannabinoid anion is not a carboxylate.

Various aspects of this patent document relate to a method to prophylactically treat a health condition, comprising administering a pharmaceutical composition comprising a therapeutically effective amount of a cannabinoid anion to a subject who presents with a risk of developing the health condition, wherein the cannabinoid anion is not a carboxylate.

"Cannabinoid anion" refers to a cannabinoid that carries a net charge of −1. As the term is used in this patent document, "cannabinoid anion" does not include carboxylates, which refer to any chemical species that comprises a carboxylate group.

"Treat" refers to at least one of: to cure a health condition; to increase the probability that a health condition will be cured; to shorten the time over which a health condition is cured; to increase the probability that the time necessary to cure a health condition will be shortened; to decrease the severity of a health condition; to increase the probability that the severity of a health condition will decrease; to shorten the time over which the severity of a health condition is decreased; to increase the probability that the time necessary to decrease the severity of a health condition will be shortened; to inhibit a health condition from worsening; to increase the probability that a health condition will not worsen; to delay the worsening of a health condition; to increase the probability that the worsening of a health condition will be delayed; to inhibit the occurrence or recurrence of a health condition; to decrease the probability that a health condition will occur or reoccur; to delay the onset of a health condition; to increase the probability that the onset of a health condition will be delayed; to alleviate at least one symptom of a health condition; to increase the probability that at least one symptom of a health condition will be alleviated; to shorten the time over which at least one symptom of a health condition is alleviated; to increase the probability that the time necessary to alleviate at least one symptom of a health condition will be shortened; to decrease the severity of at least one symptom of a health condition; to increase the probability that the severity of at least one symptom of a health condition will be decreased; to shorten the time over which the severity of at least one symptom of a health condition is decreased; to increase the probability that the time necessary to decrease the severity of at least one symptom of a health condition will be shortened; to inhibit at least one symptom of a health condition from worsening; to increase the probability that at least one symptom of a health condition will not worsen; to delay the worsening of at least one symptom of a health condition; to increase the probability that the worsening of at least one symptom of a health condition will be delayed; to inhibit at least one symptom of a health condition from occurring or reoccurring; to decrease the probability that at least one symptom of a health condition will occur or reoccur; to delay the onset of at least one symptom of a health condition; and to increase the probability that the onset of at least one symptom of a health condition will be delayed.

"Comprising" and "comprise(s)" refer to an open sets such that a pharmaceutical composition comprising a cannabinoid anion can also comprise, for example, an excipient.

In some embodiments, the method further comprises identifying that the subject presents with one or both of the health condition and a risk of developing the health condition.

In some embodiments, the health condition is type 2 diabetes mellitus. In some embodiments, the health condition is metabolic syndrome or mitochondrial disease. Cannabidiol is known to treat type 2 diabetes mellitus (see, for example, U.S. Pat. No. 8,071,641), and thus, 2-[6-isopropenyl-3-methylcyclohex-2-en-1-yl]-3-hydroxy-5-alkylphenolates and 2-[6-isopropenyl-3-methylcyclohex-3-en-1-yl]-3-hydroxy-5-alkylphenolates are particularly effective at treating both type 2 diabetes mellitus and metabolic syndrome.

In some embodiments, the health condition is obesity. Cannabinoids are known to be effective at treating obesity (see, for example, U.S. Pat. No. 9,669,002).

In some embodiments, the health condition is hypertension. In some embodiments, the health condition is pre-hypertension. A wide range of cannabinoids are effective at lowering blood pressure, and thus, the cannabinoid anions disclosed in this patent document are generally effective at treating hypertension and pre-hypertension.

In some embodiments, the health condition is a neurodegenerative disease. In some embodiments, the health condition is mild cognitive impairment, Alzheimer's Disease, Parkinson's Disease, amyotrophic lateral sclerosis ("ALS"), or Huntington's disease. Cannabidiol and cannabidivarin are effective at treating and preventing neurodegenerative diseases (see, for example, U.S. Pat. No. 10,258,580), and thus, 2-[6-isopropenyl-3-methylcyclohex-2-en-1-yl]-3-hydroxy-5-alkylphenolates and 2-[6-isopropenyl-3-methylcyclohex-3-en-1-yl]-3-hydroxy-5-alkylphenolates are particularly effective at treating neurodegenerative diseases.

In some embodiments, the health condition is an autoimmune disorder. In some embodiments, the health condition is arthritis, ankylosing spondylitis, an inflammatory autoimmune-mediated arthritis, rheumatoid arthritis, psoriatic arthritis, psoriasis, plaque psoriasis, lupus, Sjogren's syndrome, inflammatory bowel disease, Crohn's disease, or ulcerative colitis. Cannabidiol is effective at treating autoimmune disorders (see, for example, U.S. Pat. Nos. 6,410,588; 8,293,786; 9,421,187), and thus, 2-[6-isopropenyl-3-methylcyclohex-2-en-1-yl]-3-hydroxy-5-alkylphenolates and 2-[6-isopropenyl-3-methylcyclohex-3-en-1-yl]-3-hydroxy-5-alkylphenolates are particularly effective at treating autoimmune disorders.

In some embodiments, the health condition is pain. In some embodiments, the health condition is a headache, a migraine headache, or an episodic migraine. In some embodiments, the health condition is nociceptive pain; allodynia; chronic pain; intractable pain; back pain; lower back pain; chronic back pain; sciatica; spinal stenosis; chronic radiculopathy; post laminectomy syndrome; stomach pain; visceral pain; interstitial cystitis; postherpetic neuralgia; sickle cell anemia; sickle cell disease; cancer pain; intractable cancer pain; fibromyalgia; neurogenic pain; neuropathic pain; peripheral neuropathy; inflammatory demyelinating polyneuropathy; peripheral pain; reflex sympathetic dystrophy; residual limb pain; idiopathic pain; psychogenic pain; causalgia; complex regional pain syndrome; complex regional pain syndrome type I; complex regional pain syndrome type II; gout; epidermolysis bullosa; hemorrhoids; or constipation. Cannabinoids are generally effective at treating pain (see, for example, U.S. Pat. Nos. 7,968,594; 9,895,342; see also Habib et al., BRITISH JOURNAL OF ANAESTHESIA, 2019, 123(2):e249).

In some embodiments, the health condition is edema.

In some embodiments, the health condition is urinary dysfunction; overactive bladder; nephropathy; kidney disease; chronic kidney disease; renal failure requiring dialysis; pancreatitis; sepsis; heart disease; or heart failure.

In some embodiments, the health condition is elevated intraocular pressure or glaucoma.

In some embodiments, the health condition is liver disease; non-alcoholic fatty liver disease ("NAFLD"); non-alcoholic steatohepatitis ("NASH"); liver cirrhosis; decompensated cirrhosis; hepatic encephalopathy; hepatitis; autoimmune hepatitis; or hepatitis C. Cannabidiol and cannabidiol analogues are generally effective at treating liver diseases (see, for example, U.S. Pat. Nos. 10,039,724; 8,242,178), and thus, 2-[6-isopropenyl-3-methylcyclohex-2-en-1-yl]-3-hydroxy-5-alkylphenolates and 2-[6-isopropenyl-3-methylcyclohex-3-en-1-yl]-3-hydroxy-5-alkylphenolates are particularly effective at treating liver disease, non-alcoholic fatty liver disease ("NAFLD"), non-alcoholic steatohepatitis ("NASH"), liver cirrhosis, decompensated cirrhosis, hepatic encephalopathy, hepatitis, autoimmune hepatitis, and hepatitis C.

In some embodiments, the health condition is nausea; cachexia; anorexia; bulimia; vomiting; motion sickness; cancer chemotherapy-induced anorexia; human deficiency virus ("HIV") infection related nausea or cachexia; or acquired immune deficiency syndrome ("AIDS") related nausea or cachexia. Cannabinoids are known to be generally effective at treating nausea, cachexia, anorexia, bulimia, vomiting, and related conditions (see, for example, U.S. Pat. Nos. 5,605,928; 8,034,843; 8,119,697; 9,669,002; 9,675,579).

In some embodiments, the health condition is anxiety; generalized anxiety disorder; a specific phobia; agoraphobia; social anxiety disorder; separation anxiety disorder; panic disorder; selective mutism; obsessive-compulsive disorder; depression; a major depressive disorder with psychotic feature(s); psychotic depression; paranoia; psychosis; early psychosis; an unspecified psychosis; an unspecified reactive psychosis; a psychotic disorder; a brief psychotic disorder; a debilitating psychiatric disorder; schizophrenia; schizophreniform disorder; schizoaffective disorder; paranoid personality disorder; schizoid personality disorder; schizotypal personality disorder; a shared psychotic disorder; a shared paranoia disorder; a delusional disorder; bipolar disorder; bipolar I disorder; bipolar II disorder; mania; manic disorder; or manic-depressive psychosis. Cannabinoids are generally effective at treating anxiety, depression, schizophrenia, and related psychiatric disorders (see, for example, U.S. Pat. Nos. 10,441,553; 8,481,085; 8,470,874; see also Habib et al., BRITISH JOURNAL OF ANAESTHESIA, 2019, 123(2):e249, which states that a genetic condition that results in elevated endocannabinoids minimizes both anxiety and depression).

In some embodiments, the health condition is an addiction. In some embodiments, the health condition is an addiction to alcohol, tobacco, nicotine, an opiate, a stimulant, a prescription drug, gambling, food, shopping, the internet, or sex. Cannabinoids are known to be effective at treating addictions (see, for example, U.S. Pat. No. 9,669,002).

In some embodiments, the health condition is drug withdrawal; alcohol withdrawal syndrome; nicotine withdrawal; opioid withdrawal; *cannabis* withdrawal; benzodiazepine withdrawal syndrome; antidepressant discontinuation syndrome; antipsychotic withdrawal syndrome; addictive behavior; or *cannabis* use disorder.

In some embodiments, the health condition is attention deficit hyperactivity disorder ("ADHD"); autism or an autism spectrum disorder; Asperger syndrome; fragile X syndrome; a pervasive developmental disorder not otherwise specified ("PDD-NOS"); a childhood disintegrative disorder; or Tourette's syndrome.

In some embodiments, the health condition is Down syndrome. Cannabinoids are known to treat Down syndrome (see, for example, U.S. Pat. No. 8,673,368).

In some embodiments, the health condition is post-traumatic stress disorder ("PTSD").

In some embodiments, the health condition is asthma; respiratory disease; chronic lower respiratory disease; or chronic obstructive pulmonary disease ("COPD").

In some embodiments, the health condition is insomnia; sleep apnea; obstructive sleep apnea; or restless legs syndrome.

In some embodiments, the health condition is cramping; muscle spasms; spasticity; spasmodic torticollis; a dyskinetic movement disorder; dystonia; intractable spasticity; intractable skeletal muscular spasticity; inclusion body myositis; myasthenia gravis; muscular dystrophy; Duchenne muscular dystrophy; muscle tremor; cerebellar tremor; dystonic tremor; essential tremor; orthostatic tremor; Parkinsonian tremor; physiological tremor; psychogenic tremor; rubral tremor; or nystagmus. Cannabinoids are known to treat spasms, tremor, seizures, epilepsy, and health conditions that are associated with spasms, tremor, seizures, and epilepsy (see, for example, U.S. Pat. No. 9,956,186).

In some embodiments, the health condition is a seizure disorder. In some embodiments, the health condition is recurrent focal seizures; recurrent generalized seizures; recurrent absence seizures; recurrent myoclonic-absence seizures; recurrent myoclonus; recurrent myoclonic seizures; recurrent tonic seizures; recurrent tonic-clonic seizures; recurrent atonic seizures; recurrent chronic seizures; epilepsy; recurrent epileptic spasms; refractory epilepsy; intractable epilepsy; treatment-resistant epilepsy; Lennox-Gastaut syndrome; Dravet syndrome; febrile infection related epilepsy syndrome ("FIRES"); juvenile myoclonic epilepsy; myoclonic absence seizures ("MAS"); myoclonic astatic epilepsy ("MAE"); tuberous sclerosis complex ("TSC"); Rett syndrome; or Angelman syndrome. Cannabinoids are known to treat spasms, tremor, seizures, epilepsy, and health conditions that are associated with spasms, tremor, seizures, and epilepsy (see, for example, U.S. Pat. No. 9,956,186).

In some embodiments, the health condition is a neurological condition.

In some embodiments, the health condition is stroke; hemorrhagic stroke; ischemic stroke; neonatal hypoxic-ischemic encephalopathy ("NHIE"); hydrocephalus; hydromyelia; traumatic brain injury ("TBI"); post-concussion syndrome; chronic traumatic encephalopathy; a spinal cord injury; a spinal cord disease; syringomyelia; Tarlov cysts; cystic fibrosis; cerebral palsy; spinocerebellar ataxia; a neural-tube defect; neuropathy; a brain tumor; glioblastoma multiforme; glioblastoma astrocytoma; neurofibromatosis; Arnold-Chiari malformation; or multiple sclerosis.

In some embodiments, the health condition is multiple sclerosis. Cannabidiol is effective at treating multiple sclerosis (see, for example, U.S. Pat. No. 6,410,588), and thus, 2-[6-isopropenyl-3-methylcyclohex-2-en-1-yl]-3-hydroxy-5-alkylphenolates and 2-[6-isopropenyl-3-methylcyclohex-3-en-1-yl]-3-hydroxy-5-alkylphenolates are particularly effective at treating multiple sclerosis.

In some embodiments, the health condition is a connective tissue disorder.

In some embodiments, the health condition is Ehlers-Danlos syndrome; fibrous dysplasia; osteogenesis imperfecta; nail-patella syndrome; idiopathic pulmonary fibrosis; bone loss; bone loss caused by a bone fracture; bone loss caused by a surgical procedure; a periodontal defect; periodontal disease; osteopenia; an osteolytic bone disease; osteoporosis; age-related osteoporosis; hormone-related osteoporosis; hypogonadism-related osteoporosis; diabetes-related osteoporosis; glucocorticoid-related osteoporosis; disuse osteoporosis; primary hyperparathyroidism; or secondary hyperparathyroidism.

In some embodiments, the health condition is a carcinoma; sarcoma; lymphoma; leukemia; germ cell tumor; or blastoma. In some embodiments, the health condition is condition is brain cancer; ovarian cancer; breast cancer; vaginal cancer; vulvar cancer; uterine cancer; cervical cancer; endometrial cancer; prostate cancer; testicular cancer; penile cancer; liver cancer; intrahepatic bile duct cancer; lung cancer; small cell lung cancer; non-small cell lung cancer; bronchial cancer; mesothelioma; pancreatic cancer; gall bladder cancer; non-melanoma skin cancer; melanoma; Kaposi sarcoma; thyroid cancer; head and neck cancer; nasopharyngeal cancer; oropharyngeal cancer; hypopharyngeal cancer; laryngeal cancer; oral cavity cancer; tongue cancer; mouth cancer; salivary gland cancer; esophageal cancer; gastric cancer; colorectal cancer; colon cancer; rectal cancer; anal cancer; kidney cancer; renal cell cancer; renal pelvis cancer; bladder cancer; urethral cancer; Hodgkin lymphoma; non-Hodgkin's lymphoma; myeloma; multiple myeloma; acute lymphocytic leukemia; chronic lymphocytic leukemia; acute myeloid leukemia; chronic myeloid leukemia; osteosarcoma; or soft tissue cancer. Cannabinoids are known to be generally effective at treating a wide range of cancers including bladder cancer (see, for example, U.S. Pat. No. 9,962,341), brain cancer (see, for example, U.S. Pat. No. 9,084,771), breast cancer (see, for example, U.S. Pat. Nos. 9,962,341; 9,675,654), colon cancer (see, for example, U.S. Pat. No. 9,675,654), gastric cancer (see, for example, U.S. Pat. No. 9,962,341), gliomas (see, for example, U.S. Pat. No. 8,790,719), liver cancer (see, for example, U.S. Pat. No. 9,962,341), lung cancer (see, for example, U.S. Pat. No. 9,962,341; see also Sulé-Suso et al. SAGE OPEN MEDICAL CASE REPORTS, 2019, 7:1-4), melanomas (see, for example, U.S. Pat. No. 9,962,341), ovarian cancer (see, for example, U.S. Pat. No. 10,098,867), pancreatic cancer (see, for example, U.S. Pat. No. 9,962,341), prostate cancer (see, for example, U.S. Pat. No. 9,675,654), and renal cell cancer (see, for example, U.S. Pat. No. 9,962,341).

In some embodiments, at least one symptom of the health condition is pain; and the pharmaceutical composition is administered to treat pain.

In some embodiments, at least one symptom of the health condition is inflammation; and the pharmaceutical composition is administered to treat inflammation.

In some embodiments, at least one symptom of the health condition is anxiety; and the pharmaceutical composition is administered to treat anxiety.

In some embodiments, the subject presents with both the health condition and hypertension; hypertension exacerbates the health condition; and the pharmaceutical composition is administered to treat the hypertension.

In some embodiments, the subject presents with both the health condition and pre-hypertension; either pre-hypertension or hypertension exacerbates the health condition; and the pharmaceutical composition is administered to either treat the pre-hypertension or reduce the risk that the subject will develop hypertension.

In some embodiments, at least one symptom of the health condition is edema; and the pharmaceutical composition is administered to increase diuresis.

In some embodiments, diuretic properties of the cannabinoid anion treat the health condition.

In some embodiments, the health condition is an autoimmune disease; and the pharmaceutical composition is administered to inhibit an immune response in the subject.

In some embodiments, tumor necrosis factor alpha ("TNF-alpha") signaling either causes or exacerbates the health condition; and the pharmaceutical composition is administered to inhibit TNF-alpha-mediated signaling pathways.

In some embodiments, interleukin 10 ("IL-10") signaling either causes or exacerbates the health condition; and the pharmaceutical composition is administered to modulate IL-10-mediated signaling pathways.

In some embodiments, interferon gamma ("INF-gamma") signaling either causes or exacerbates the health condition; and the pharmaceutical composition is administered to modulate INF-gamma-mediated signaling pathways.

In some embodiments, at least one symptom of the health condition is muscle cramping, spasticity, tremor, or muscle spasms; and the pharmaceutical composition is administered to treat the muscle cramping, spasticity, tremor, or muscle spasms.

In some embodiments, at least one symptom of the health condition is seizures; and the pharmaceutical composition is administered to treat seizures.

In some embodiments, at least one symptom of the health condition is appetite suppression, nausea, or vomiting; and the pharmaceutical composition is administered to treat the appetite suppression, nausea, or vomiting.

In some embodiments, the subject is receiving a primary pharmaceutical agent to treat the health condition; the primary pharmaceutical agent causes appetite suppression, nausea, or vomiting; and the pharmaceutical composition is administered to treat the appetite suppression, nausea, or vomiting.

In some embodiments, at least one symptom of the health condition is decreased bone density; and the pharmaceutical composition is administered to treat bone loss.

In some embodiments, the health condition is a terminal illness; and the pharmaceutical composition is administered to provide palliative care.

In some embodiments, the administering is performed by a pharmacist by dispensing the pharmaceutical composition to either the subject, a family member of the subject, a caregiver of the subject, or another agent of the subject.

In some embodiments, the administering is performed by a healthcare professional by either prescribing the pharmaceutical composition to the subject or prescribing the cannabinoid anion to the subject.

In some embodiments, the administering is performed by either the subject or a caregiver of the subject by directing the pharmaceutical composition either into the body of the subject or onto the body of the subject.

In some embodiments, the administering is enteral; oral; rectal; sublingual; sublabial; buccal; intranasal; inhalational; transmucosal; topical; transdermal; intravenous; intramuscular; subcutaneous; intradermal; intraocular; parenteral; intrathecal; intralesional; or intratumoral administration.

In some embodiments, the pharmaceutical composition is a liquid; beverage; elixir; tincture; syrup; pill; tablet; capsule; gel cap; soft gel; gummy; gel; cream; lotion; balm; salve; ointment; dermal patch; transdermal patch; powder; or suppository.

In some embodiments, the subject is a human.

In some embodiments, the subject is a chicken, rodent, lagomorph, feline, canine, porcine, ovine, caprine, *lama, vicugna*, bovine, *equine*, or primate.

In some embodiments, the cannabinoid anion is selected from 2-(3,7-dimethylocta-2,6-diene-1-yl)-3-hydroxy-5-alkylphenolate; 2-(6-isopropenyl-3-methylcyclohex-2-en-1-yl)-3-hydroxy-5-alkylphenolate; 2-(6-isopropenyl-3-methylcyclohex-3-en-1-yl)-3-hydroxy-5-alkylphenolate; 2-(6-isopropenyl-3-methylcyclohex-2-en-1-yl)-5-alkyl-1,4-benzoquinone-3-oxide; 2-(6-isopropenyl-3-methylcyclohex-3-en-1-yl)-5-alkyl-1,4-benzoquinone-3-oxide; 3-(6-isopropenyl-3-methylcyclohex-2-en-1-yl)-6-alkyl-1,2-benzoquinone-4-oxide; 3-(6-isopropenyl-3-methylcyclohex-3-en-1-yl)-6-alkyl-1,2-benzoquinone-4-oxide; 6,6,9-trimethyl-3-alkyl-6a,7,8,10a-tetrahydro-6H-benzo[c]chromen-1-oxide; 6,6,9-trimethyl-3-alkyl-6a,7,10,10a-tetrahydro-6H-benzo[c]chromen-1-oxide; 6,6,9-trimethyl-3-alkyl-7,8,9,10-tetrahydro-6H-benzo[c]chromen-1-oxide; 3-alkyl-6,6-dimethyl-9-hydroxymethyl-6a,7,8,10a-tetrahydro-6H-benzo[c]chromen-1-oxide; 3-alkyl-6,6-dimethyl-9-hydroxymethyl-6a,7,10,10a-tetrahydro-6H-benzo[c]chromen-1-oxide; 3-alkyl-6,6-dimethyl-9-hydroxymethyl-7,8,9,10-tetrahydro-6H-benzo[c]chromen-1-oxide; 3-alkyl-6,6-dimethyl-9-formyl-6a,7,8,10a-tetrahydro-6H-benzo[c]chromen-1-oxide; 3-alkyl-6,6-dimethyl-9-formyl-6a,7,10,10a-tetrahydro-6H-benzo[c]chromen-1-oxide; 3-alkyl-6,6-dimethyl-9-formyl-7,8,9,10-tetrahydro-6H-benzo[c]chromen-1-oxide; 2-methyl-2-(4-methylpent-3-en-1-yl)-7-alkyl-2H-1-benzopyran-5-oxide; 3-alkyl-6,6-dimethyl-9-methyl-6a,7,8,9,10,10a-hexahydro-6H-benzo[c]chromen-1-oxide; 3-alkyl-6,6-dimethyl-9-hydroxymethyl-6a,7,8,9,10,10a-hexahydro-6H-benzo[c]chromen-1-oxide; 3-alkyl-6,6-dimethyl-9-formyl-6a,7,8,9,10,10a-hexahydro-6H-benzo[c]chromen-1-oxide; 3-alkyl-6,6-dimethyl-9-oxo-6,6a,7,8,10,10a-hexahydro-9H-benzo[c]chromen-1-oxide; and 3-alkyl-6,6-dimethyl-9-hydroxy-6a,7,8,9,10,10a-hexahydro-6H-benzo[c]chromen-1-oxide. In some specific embodiments, the cannabinoid is 2-(3,7-dimethylocta-2,6-diene-1-yl)-3-hydroxy-5-alkylphenolate. In some specific embodiments, the cannabinoid is 2-(6-isopropenyl-3-methylcyclohex-2-en-1-yl)-3-hydroxy-5-alkylphenolate. In some specific embodiments, the cannabinoid is 6,6,9-trimethyl-3-alkyl-7,8,9,10-tetrahydro-6H-benzo[c]chromen-1-oxide.

"Alkyl" refers to a branched or unbranched hydrocarbon chain comprising exactly 1, 2, 3, 4, 5, 6, 7, 8, 9, 10, 11, or 12 carbon atoms that is optionally substituted by phenyl or cycloalkyl. Alkyl species are generally similarly effective at treating the indications that either a pentyl or propyl species is effective at treating. For example, 2-(6-isopropenyl-3-methylcyclohex-2-en-1-yl)-3-hydroxy-5-alkylphenolates are generally as effective at treating the same indications that 2-(6-isopropenyl-3-methylcyclohex-2-en-1-yl)-3-hydroxy-5-pentylphenolate is effective at treating.

"Substituted by phenyl or cycloalkyl" refers to the substitution of one hydrogen atom of a hydrocarbon chain with phenyl or the substitution of at least one hydrogen atom of a hydrocarbon chain with a cycloalkyl, respectively. When a hydrocarbon chain is substituted with a cycloalkyl, then either (i) a single hydrogen atom of the hydrocarbon chain is substituted with the cycloalkyl such that the cycloalkyl does not include any carbon atom of the hydrocarbon chain, or (ii) two hydrogen atoms of the hydrocarbon chain are substituted with the cycloalkyl such that the cycloalkyl comprises one or more carbon atoms of the hydrocarbon chain. The carbon atoms of phenyl or cycloalkyl are counted when counting the carbon atoms of a hydrocarbon chain that is substituted by phenyl or cycloalkyl, for example, such that 2-phenylethyl comprises exactly 8 carbon atoms and adamantyl comprises exactly 10 carbon atoms.

"Cycloalkyl" refers to cyclopropyl, cyclobutyl, cyclopentyl, cyclohexyl, cycloheptyl, and adamantyl.

In some embodiments, the cannabinoid anion is selected from 2-(6-isopropenyl-3-halomethylcyclohex-2-en-1-yl)-3-hydroxy-5-alkylphenolate; 2-(6-isopropenyl-3-halomethylcyclohex-3-en-1-yl)-3-hydroxy-5-alkylphenolate; 3-alkyl-6,6-dimethyl-9-halomethyl-6a,7,8,10a-tetrahydro-6H-benzo[c]chromen-1-oxide; 3-alkyl-6,6-dimethyl-9-halomethyl-6a,7,10,10a-tetrahydro-6H-benzo[c]chromen-1-oxide; 3-alkyl-6,6-dimethyl-9-halomethyl-7,8,9,10-tetrahydro-6H-benzo[c]chromen-1-oxide; and 3-alkyl-6,6-dimethyl-9-halomethyl-6a,7,8,9,10,10a-hexahydro-6H-benzo[c]chromen-1-oxide.

"Halomethyl" refers to fluoromethyl, chloromethyl, bromomethyl, and iodomethyl. In some specific embodiments, halomethyl is fluoromethyl.

In some embodiments, alkyl is methyl; ethyl; propyl; butyl; pentyl; hexyl; heptyl; octyl; nonyl; decyl; prop-2-yl; but-2-yl; pent-2-yl; hex-2-yl; hept-2-yl; octan-2-yl; nonan-2-yl; decan-2-yl; 2-methylpropyl; 2-methylbutyl; 2-methylpentyl; 2-methylhexyl; 2-methylheptyl; 2-methyloctyl; 2-methylnonyl; 2-methyldecyl; 2-methylprop-2-yl; 2-methylbut-2-yl; 2-methylpent-2-yl; 2-methylhex-2-yl; 2-methylhept-2-yl; 2-methyloctan-2-yl; 2-methylnonan-2-yl; 2-methyldecan-2-yl; 3-methylbut-2-yl; 3-methylpent-2-yl; 3-methylhex-2-yl; 3-methylhept-2-yl; 3-methyloctan-2-yl; 3-methylnonan-2-yl; 3-methyldecan-2-yl; 2,3-dimethylbut-2-yl; 2,3-dimethylpent-2-yl; 2,3-dimethylhex-2-yl; 2,3-dimethylhept-2-yl; 2,3-dimethyloctan-2-yl; 2,3-dimethylnonan-2-yl; 2,3-dimethyldecan-2-yl; cyclopropyl; 1-methylcyclopropyl; 1-ethylcyclopropyl; 1-propylcyclopropyl; 1-butylcyclopropyl; 1-pentylcyclopropyl; 1-hexylcyclopropyl; 1-heptylcyclopropyl; 1-octylcyclopropyl; 1-nonylcyclopropyl; cyclobutyl; 1-methylcyclobutyl; 1-ethylcyclobutyl; 1-propylcyclobutyl; 1-butylcyclobutyl; 1-pentylcyclobutyl; 1-hexylcyclobutyl; 1-heptylcyclobutyl; 1-octylcyclobutyl; cyclopentyl; 1-methylcyclopentyl; 1-ethylcyclopentyl; 1-propylcyclopentyl; 1-butylcyclopentyl; 1-pentylcyclopentyl; 1-hexylcyclopentyl; 1-heptylcyclopentyl; cyclohexyl; 1-methylcyclohexyl; 1-ethylcyclohexyl; 1-propylcyclohexyl; 1-butylcyclohexyl; 1-pentylcyclohexyl; 1-hexylcyclohexyl; ethenyl; prop-1-enyl; but-1-enyl; pent-1-enyl; hex-1-enyl; hept-1-enyl; octan-1-enyl; nonan-1-enyl; decan-1-enyl; ethynyl; prop-1-ynyl; but-1-ynyl; pent-1-ynyl; hex-1-ynyl; hept-1-ynyl; octan-1-ynyl; nonan-1-ynyl; decan-1-ynyl; 2-phenylethyl; or adamantyl. In some specific embodiments, alkyl is methyl, ethyl, propyl, butyl, pentyl, hexyl, or heptyl. In some very specific embodiments, alkyl is propyl. In some very specific embodiments, alkyl is pentyl.

In some embodiments, the therapeutically effective amount of the cannabinoid anion is at least 10 micrograms and no greater than 10 grams. In some specific embodiments, the therapeutically effective amount of the cannabinoid anion is at least 100 micrograms and no greater than 1 gram. In some very specific embodiments, the therapeutically effective amount of the cannabinoid anion is at least 1 milligram and no greater than 100 milligrams.

In some embodiments, the pharmaceutical composition comprises one, two, three, or each of hydroxide, ethoxide, 1,3-dihydroxypropane-2-oxide, and 2,3-dihydroxypropane-1-oxide. In some specific embodiments, the pharmaceutical composition comprises hydroxide. In some specific embodiments, the pharmaceutical composition comprises ethoxide. In some specific embodiments, the pharmaceutical composition comprises one or both of 1,3-dihydroxypropane-2-oxide and 2,3-dihydroxypropane-1-oxide. In some very specific embodiments, the pharmaceutical composition comprises hydroxide and ethoxide. In some even more specific embodiments, the pharmaceutical composition comprises each of hydroxide, ethoxide, 1,3-dihydroxy-propane-2-oxide, and 2,3-dihydroxy-propane-1-oxide.

In some embodiments, the pharmaceutical composition comprises one, two, or each of water, ethanol, and glycerol.

In some embodiments, the pharmaceutical composition comprises sodium cation (Na+).

In some embodiments, the pharmaceutical composition comprises potassium cation (K+).

EXEMPLIFICATION

The examples set forth specific embodiments of this disclosure, and the examples do not limit the scope of the disclosure or any claim that matures from this patent document.

Example 1. Treatment of Cancer Pain

An individual who presented with cancer pain caused by throat cancer was administered water containing the cannabidiol anion (2-[6-isopropenyl-3-methylcyclohex-2-en-1-yl]-3-hydroxy-5-pentylphenolate). The individual reported notable alleviation of throat pain within minutes of ingestion.

Example 2. Treatment of Acute Back Pain

An individual who presented with back pain associated with driving for prolonged periods of time was administered a glycerol tincture containing the cannabidiol anion. The individual reported notable alleviation of the back pain within minutes of ingestion.

Example 3. Treatment of Chronic Back Pain

An individual who presented with chronic back pain associated with standing was administered a glycerol tincture containing the cannabidiol anion. The individual reported notable alleviation of the back pain within minutes of ingestion.

Example 4. Treatment of Chronic Hip Pain

An individual who presented with hip pain associated with sitting was administered a glycerol tincture containing the cannabidiol anion. The individual reported notable alleviation of the hip pain within minutes of ingestion.

Example 5. Treatment of Post Laminectomy Syndrome

An 87-year-old individual with hip pain and lower back pain associated with spinal fusion surgery was administered a glycerol tincture containing the cannabidiol anion. The individual reported notable alleviation of hip pain and lower back pain within minutes of ingestion.

Example 6. Treatment of Knee Pain

An individual who presented with knee pain associated with inflammation caused by trauma from a fall was administered a glycerol tincture containing the cannabidiol anion. The individual reported improved mobility and alleviation of knee pain within minutes of ingestion.

Example 7. Treatment of Arthritis

An individual who was unable to fill her hydroxychloroquine prescription to treat the arthritis during the COVID-19 pandemic was administered a glycerol tincture containing the cannabidiol anion. The individual reported that the glycerol tincture containing the cannabidiol anion was more effective at treating her arthritis than hydroxychloroquine.

Example 8. Treatment of Chronic Pain

An individual who presented with chronic pain was administered a glycerol tincture containing the cannabidiol anion. The individual reported significant improvement in her standard of living.

Example 9. Treatment of Anxiety

An individual was administered a beverage containing the cannabidiol anion prior to driving to an airport to catch a flight that was scheduled to leave within thirty minutes of the arrival at the airport. The individual reported that he would ordinarily experience anxiety during such a drive when confronted with a similar timeline, and the individual reported a notable absence of anxiety.

An individual who suffers from chronic anxiety was administered a glycerol tincture containing the cannabigerol anion. The individual reported a significant improvement in his anxiety symptoms.

Example 10. Treatment of Social Anxiety

An individual who presented with social anxiety associated with presenting at business meetings was administered a beverage containing the cannabidiol anion before presenting. The individual reported reduced anxiety and improved performance during the business meeting.

Example 11. Treatment of Cramping and Restless Legs Syndrome

An individual who presented with cramping and restless legs syndrome was administered a glycerol tincture containing the cannabidiol anion before sleep. The individual reported a significant improvement in sleep quality. The individual noted similar improvements after taking a glycerol tincture containing the cannabigerol anion (2-[3,7-dimethylocta-2,6-diene-1-yl]-3-hydroxy-5-pentylphenolate) before sleep.

Example 12. Treatment of Epilepsy

A dog that suffers from chronic seizures was administered a glycerol tincture containing the cannabidiol anion immediately after the onset of a seizure. The owners of the dog reported that the glycerol tincture containing the cannabidiol anion both instantaneously and consistently arrested multiple seizures in the dog and significantly improved the dog's quality of life.

Example 13. Treatment of Insomnia

An individual who presented with chronic insomnia was administered a glycerol tincture containing the cannabigerol anion before sleep. The individual reported a significant improvement in the onset and quality of his sleep.

Example 14. Treatment of Crohn's Disease

An individual who presented with Crohn's disease was administered a glycerol tincture containing the cannabigerol anion. The individual reported a significant improvement in her symptoms of Crohn's disease, which enabled here to eat problem foods that she could not previously eat without debilitating gastrointestinal distress.

Example 15. Treatment of Inflammatory Bowel Disease

An individual who presented with Inflammatory Bowel Disease was administered a glycerol tincture containing the cannabigerol anion. The individual reported a significant improvement in her symptoms of Inflammatory Bowel Disease, which enabled here to eat problem foods that she could not previously eat without debilitating gastrointestinal distress.

What is claimed is:

1. A method to administer a cannabinoid anion, comprising administering a pharmaceutical composition comprising a cannabinoid anion to a subject who presents with either a health condition or a risk of developing a health condition, wherein the cannabinoid anion is not a carboxylate, and wherein the health condition is arthritis, ankylosing spondylitis, an inflammatory autoimmune-mediated arthritis, rheumatoid arthritis, psoriatic arthritis, psoriasis, plaque psoriasis, lupus, Sjogren's syndrome, inflammatory bowel disease, Crohn's disease, ulcerative colitis, pain, nociceptive pain, allodynia, chronic pain, intractable pain, back pain, lower back pain, chronic back pain, sciatica, spinal stenosis, chronic radiculopathy, post laminectomy syndrome, stomach pain, visceral pain, interstitial cystitis, postherpetic neuralgia, sickle cell anemia, sickle cell disease, cancer pain, intractable cancer pain, fibromyalgia, neurogenic pain, neuropathic pain, peripheral neuropathy, inflammatory demyelinating polyneuropathy, peripheral pain, reflex sympathetic dystrophy, residual limb pain, idiopathic pain, psychogenic pain, causalgia, complex regional pain syndrome, complex regional pain syndrome type I, complex regional pain syndrome type II, gout, epidermolysis bullosa, hemorrhoids, or constipation.

2. A method to treat a health condition, comprising administering a pharmaceutical composition comprising a therapeutically effective amount of a cannabinoid anion to a subject who presents with the health condition, wherein the cannabinoid anion is not a carboxylate, and wherein the health condition is arthritis, ankylosing spondylitis, an inflammatory autoimmune-mediated arthritis, rheumatoid arthritis, psoriatic arthritis, psoriasis, plaque psoriasis, lupus, Sjogren's syndrome, inflammatory bowel disease, Crohn's disease, ulcerative colitis, pain, nociceptive pain, allodynia, chronic pain, intractable pain, back pain, lower back pain, chronic back pain, sciatica, spinal stenosis, chronic radiculopathy, post laminectomy syndrome, stomach pain, visceral pain, interstitial cystitis, postherpetic neuralgia, sickle cell anemia, sickle cell disease, cancer pain, intractable cancer pain, fibromyalgia, neurogenic pain, neuropathic pain, peripheral neuropathy, inflammatory demyelinating polyneuropathy, peripheral pain, reflex sympathetic dystrophy, residual limb pain, idiopathic pain, psychogenic pain, causalgia, complex regional pain syndrome, complex regional pain syndrome type I, complex regional pain syndrome type II, gout, epidermolysis bullosa, hemorrhoids, or constipation.

3. A method to prophylactically treat a health condition, comprising administering a pharmaceutical composition comprising a therapeutically effective amount of a cannabinoid anion to a subject who presents with a risk of developing the health condition, wherein the cannabinoid anion is not a carboxylate, and wherein the health condition is arthritis, ankylosing spondylitis, an inflammatory autoimmune-mediated arthritis, rheumatoid arthritis, psoriatic arthritis, psoriasis, plaque psoriasis, lupus, Sjogren's syndrome, inflammatory bowel disease, Crohn's disease, ulcerative colitis, pain, nociceptive pain, allodynia, chronic pain, intractable pain, back pain, lower back pain, chronic back pain, sciatica, spinal stenosis, chronic radiculopathy, post laminectomy syndrome, stomach pain, visceral pain, interstitial cystitis, postherpetic neuralgia, sickle cell anemia, sickle cell disease, cancer pain, intractable cancer pain, fibromyalgia, neurogenic pain, neuropathic pain, peripheral neuropathy, inflammatory demyelinating polyneuropathy, peripheral pain, reflex sympathetic dystrophy, residual limb pain, idiopathic pain, psychogenic pain, causalgia, complex regional pain syndrome, complex regional pain syndrome type I, complex regional pain syndrome type II, gout, epidermolysis bullosa, hemorrhoids, or constipation.

4. The method of claim 1, wherein the health condition is arthritis, ankylosing spondylitis, an inflammatory autoimmune-mediated arthritis, rheumatoid arthritis, psoriatic arthritis, psoriasis, plaque psoriasis, lupus, Sjogren's syndrome, inflammatory bowel disease, Crohn's disease, or ulcerative colitis.

5. The method of claim 1, wherein the health condition is pain.

6. The method of claim 1, wherein the health condition is nociceptive pain; allodynia; chronic pain; intractable pain; back pain; lower back pain;

chronic back pain; sciatica; spinal stenosis; chronic radiculopathy; post laminectomy syndrome; stomach pain; visceral pain; interstitial cystitis; postherpetic neuralgia;

sickle cell anemia; sickle cell disease; cancer pain; intractable cancer pain;

fibromyalgia; neurogenic pain; neuropathic pain; peripheral neuropathy; inflammatory demyelinating polyneuropathy; peripheral pain; reflex sympathetic dystrophy; residual limb pain; idiopathic pain; psychogenic pain; causalgia; complex regional pain syndrome; complex regional pain syndrome type I; complex regional pain syndrome type II; gout; epidermolysis bullosa; hemorrhoids; or constipation.

7. The method of claim 1, wherein tumor necrosis factor alpha ("TNF-alpha") signaling either causes or exacerbates the health condition; and
the pharmaceutical composition is administered to inhibit TNF-alpha-mediated signaling pathways.

8. The method of claim 1, wherein the administering is enteral; oral; rectal; sublingual; sublabial; buccal; intranasal; inhalational;
transmucosal; topical; transdermal; intravenous; intramuscular; subcutaneous;
intradermal; intraocular; parenteral; intrathecal; intralesional; or intratumoral administration.

9. The method of claim 1, wherein the cannabinoid is 2-(3,7-dimethylocta-2,6-diene-1-yl)-3-hydroxy-5-alkylphenolate.

10. The method of claim 1, wherein the cannabinoid anion is 2-(3,7-dimethylocta-2,6-diene-1-yl)-3-hydroxy-5-propylphenolate or 2-(3,7-dimethylocta-2,6-diene-1-yl)-3-hydroxy-5-pentylphenolate.

11. The method of claim 1, wherein:
the health condition is peripheral neuropathy; and
the cannabinoid anion is 2-(3,7-dimethylocta-2,6-diene-1-yl)-3-hydroxy-5-alkylphenolate.

12. The method of claim 11, wherein the administering is topical administering.

13. The method of claim 1, wherein:
the condition is psoriatic arthritis, psoriasis, or plaque psoriasis; and
the cannabinoid anion is 2-(3,7-dimethylocta-2,6-diene-1-yl)-3-hydroxy-5-alkylphenolate.

14. The method of claim 13, wherein the administering is topical administering.

15. The method of claim 1, wherein:
the condition is arthritis, an inflammatory autoimmune-mediated arthritis, rheumatoid arthritis, or psoriatic arthritis; and
the cannabinoid anion is 2-(3,7-dimethylocta-2,6-diene-1-yl)-3-hydroxy-5-alkylphenolate.

16. The method of claim 15, wherein the administering is topical administering.

17. The method of claim 1, wherein:
tumor necrosis factor alpha ("TNF-alpha") signaling either causes or exacerbates the health condition;
the pharmaceutical composition is administered to inhibit TNF-alpha-mediated signaling pathways; and
the cannabinoid anion is 2-(3, 7-dimethylocta-2,6-diene-1-yl)-3-hydroxy-5-alkylphenolate.

18. The method of claim 17, wherein the administering is topical administering.

19. The method of claim 1, wherein
the condition is pain; and
the administering is topical administering.

20. The method of claim 19, wherein the cannabinoid anion is 2-(3,7-dimethylocta-2,6-diene-1-yl)-3-hydroxy-5-alkylphenolate.

* * * * *